(12) United States Patent
Lim et al.

(10) Patent No.: US 9,786,847 B2
(45) Date of Patent: Oct. 10, 2017

(54) COMPOUND FOR ORGANIC PHOTOELECTRIC DEVICE, AND ORGANIC PHOTOELECTRIC DEVICE AND IMAGE SENSOR INCLUDING THE SAME

(71) Applicant: Samsung Electronics Co., Ltd., Suwon-si, Gyeonggi-do (KR)

(72) Inventors: Seon-Jeong Lim, Yongin-si (KR); Sung Young Yun, Suwon-si (KR); Takkyun Ro, Hwaseong-si (KR); Yong Wan Jin, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/942,562

(22) Filed: Nov. 16, 2015

(65) Prior Publication Data

US 2016/0155954 A1    Jun. 2, 2016

(30) Foreign Application Priority Data

Nov. 25, 2014  (KR) .......................... 10-2014-0165398

(51) Int. Cl.
| | | |
|---|---|---|
| *C07D 421/06* | (2006.01) | |
| *C07D 409/06* | (2006.01) | |
| *H01L 27/30* | (2006.01) | |
| *H01L 51/00* | (2006.01) | |
| *H01L 51/42* | (2006.01) | |

(52) U.S. Cl.
CPC ........ *H01L 51/0061* (2013.01); *C07D 409/06* (2013.01); *C07D 421/06* (2013.01); *H01L 27/307* (2013.01); *H01L 51/006* (2013.01); *H01L 51/0062* (2013.01); *H01L 51/0067* (2013.01); *H01L 51/0068* (2013.01); *H01L 51/4253* (2013.01)

(58) Field of Classification Search
CPC . H01L 51/0061; H01L 27/307; H01L 51/006; H01L 51/447; C07D 409/06; C07D 421/06
USPC .............................. 257/40; 546/268.1, 281.4
See application file for complete search history.

(56) References Cited

U.S. PATENT DOCUMENTS

| | | |
|---|---|---|
| 5,389,596 A | 2/1995 | Etzbach et al. |
| 5,580,980 A | 12/1996 | Etzbach et al. |
| 5,654,122 A | 8/1997 | Etzbach et al. |
| 5,719,288 A | 2/1998 | Sens et al. |

(Continued)

FOREIGN PATENT DOCUMENTS

| | | |
|---|---|---|
| EP | 0529162 A1 | 3/1993 |
| JP | 05-117542 | 5/1993 |

(Continued)

OTHER PUBLICATIONS

Frank Wuerthner et al., "ATOP Dyes. Optimization of Multifunctional Merocyanine Chromophore for High Refractive Index Modulation in Photorefractive Materials", 2001, American Chemical Society, vol. 123, No. 12, pp. 2810-2824.

*Primary Examiner* — Noble Jarrell
*Assistant Examiner* — Daniel Carcanague
(74) *Attorney, Agent, or Firm* — Harness, Dickey & Pierce, P.L.C.

(57) ABSTRACT

A compound for an organic photoelectric device is represented by Chemical Formula 1, and an organic photoelectric device, an image sensor, and an electronic device include the same.

18 Claims, 9 Drawing Sheets

(56) References Cited

U.S. PATENT DOCUMENTS

| | | | |
|---|---|---|---|
| 2003/0209651 A1* | 11/2003 | Iwasaki | H01L 27/302 250/214.1 |
| 2009/0140123 A1* | 6/2009 | Shen | H01L 27/307 250/206 |
| 2010/0140559 A1* | 6/2010 | Klaus | B82Y 10/00 252/501.1 |
| 2011/0074491 A1 | 3/2011 | Yofu et al. | |
| 2011/0256422 A1* | 10/2011 | Reichelt | B82Y 10/00 428/704 |
| 2016/0020401 A1* | 1/2016 | Bulliard | H01L 51/0058 257/40 |
| 2016/0111651 A1* | 4/2016 | Yun | H01L 51/4253 257/40 |
| 2016/0126470 A1* | 5/2016 | Ro | H01L 51/0053 257/40 |
| 2016/0146727 A1* | 5/2016 | Choi | G01N 21/3103 356/432 |
| 2016/0149132 A1* | 5/2016 | Lim | H01L 51/006 257/40 |

FOREIGN PATENT DOCUMENTS

| | | |
|---|---|---|
| JP | 06-041459 | 2/1994 |
| JP | 07261331 | * 10/1995 |
| JP | 3117712 | 10/2000 |
| WO | WO 2015122567 | * 8/2015 |

* cited by examiner

COMPOUND FOR ORGANIC PHOTOELECTRIC DEVICE, AND ORGANIC PHOTOELECTRIC DEVICE AND IMAGE SENSOR INCLUDING THE SAME

CROSS REFERENCE TO RELATED APPLICATION

This application claims the benefit of priority from Korean Patent Application No. 10-2014-0165398 filed in the Korean Intellectual Property Office on Nov. 25, 2014, the entire contents of which are incorporated herein by reference.

BACKGROUND

1. Field

Example embodiments relate to a compound for an organic photoelectric device, and an organic photoelectric device and an image sensor including the same.

2. Description of the Related Art

A photoelectric device converts light into an electrical signal using photoelectric effects, and may include a photodiode and/or a phototransistor. The photoelectric device may be applied to an image sensor, a solar cell and/or an organic light emitting diode.

An image sensor including a photodiode requires relatively high resolution and thus a relatively small pixel. At present, a silicon photodiode is widely used, but the silicon photodiode has a problem of deteriorated sensitivity and has a relatively small absorption area due to relatively small pixels. Accordingly, an organic material that is capable of replacing silicon has been researched.

The organic material has a relatively high extinction coefficient and selectively absorbs light in a particular wavelength region depending on a molecular structure, and thus may simultaneously replace a photodiode and a color filter and resultantly improve sensitivity and contribute to relatively high integration.

SUMMARY

Example embodiments provide a compound for an organic photoelectric device being capable of selectively absorbing light in a green wavelength region.

Example embodiments also provide an organic photoelectric device being capable of selectively absorbing light in a green wavelength region and improving efficiency.

Example embodiments also provide an image sensor including the organic photoelectric device.

Example embodiments also provide an electronic device including the image sensor.

According to example embodiments, a compound for an organic photoelectric device is represented by Chemical Formula 1.

[Chemical Formula 1]

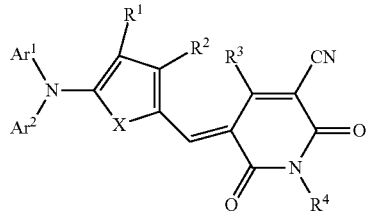

In Chemical Formula 1,

X is one of S, Se, Te, S(=O), S(=O)$_2$, and SiR$^a$R$^b$ (wherein each of R$^a$ and R$^b$ are one of hydrogen and a C$_1$ to C$_6$ alkyl group), each of Ar$^1$ and Ar$^2$ are independently one of a substituted or unsubstituted C$_6$ to C$_{30}$ aryl group and a substituted or unsubstituted C$_4$ to C$_{20}$ heteroaryl group, each of R$^1$ and R$^2$ are independently one of hydrogen, a substituted or unsubstituted C$_1$ to C$_6$ alkyl group, a substituted or unsubstituted C$_6$ to C$_{10}$ aryl group, and a substituted or unsubstituted C$_4$ to C$_8$ heteroaryl group, and each of R$^3$ and R$^4$ are independently one of a substituted or unsubstituted C$_1$ to C$_6$ alkyl group and a substituted or unsubstituted C$_6$ to C$_{10}$ aryl group.

The compound may have 6 or 7 aromatic rings.

At least one of Ar$^1$ and Ar$^2$ may be one of a naphthyl group and an anthracenyl group.

The compound may have a maximum absorption wavelength ($\lambda_{max}$) of about 500 nm to about 600 nm.

The compound may show a light absorption curve having a full width at half maximum (FWHM) in a thin film state of about 50 nm to about 130 nm.

The compound may show a light absorption curve having a full width at half maximum (FWHM) in a thin film state of about 50 nm to about 100 nm.

The compound may be a p-type semiconductor compound.

According to example embodiments, an organic photoelectric device includes a first electrode and a second electrode facing each other, and an active layer between the first electrode and the second electrode and including the compound represented by Chemical Formula 1.

According to example embodiments, an image sensor includes the organic photoelectric device.

The image sensor may include a semiconductor substrate integrated with a plurality of first photo-sensing devices sensing light in a blue wavelength region and a plurality of second photo-sensing devices sensing light in a red wavelength region, wherein the organic photoelectric device is on the semiconductor substrate and selectively absorbs light in a green wavelength region.

The plurality of first photo-sensing devices and the plurality of second photo-sensing devices may be stacked in a vertical direction on the semiconductor substrate.

The image sensor may further include a color filter layer between the semiconductor substrate and the organic photoelectric device, and including a blue filter selectively absorbing light in a blue wavelength region and a red filter selectively absorbing light in a red wavelength region.

The organic photoelectric device may be a green photoelectric device, and the image sensor may further include a blue photoelectric device selectively absorbing light in a blue wavelength region, and a red photoelectric device selectively absorbing light in a red wavelength region, wherein the organic photoelectric device, a blue photoelectric device and a red photoelectric device may be sequentially stacked.

According to example embodiments, an electronic device includes the image sensor.

DETAILED DESCRIPTION

Figure 1:
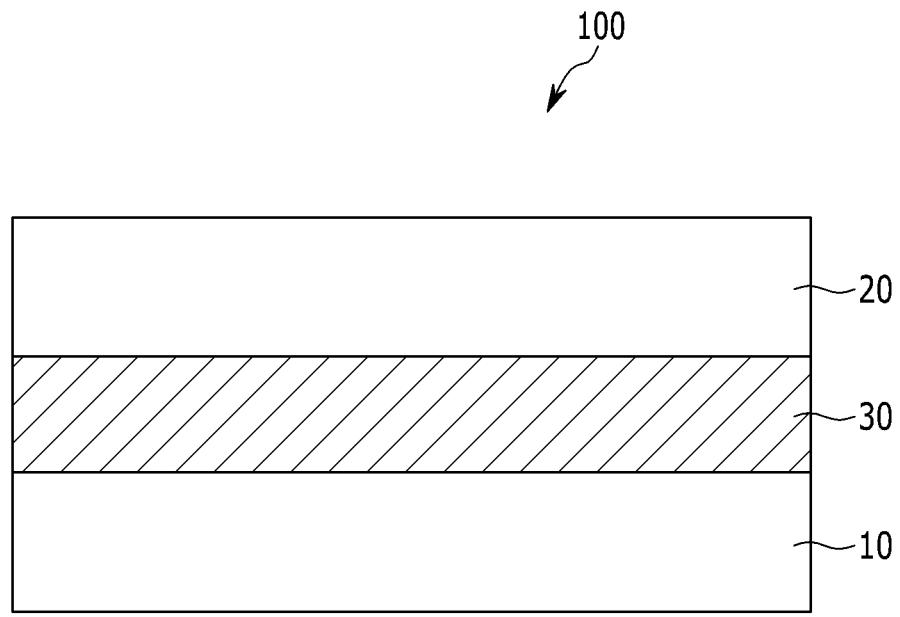
FIG. 1 is a cross-sectional view showing an organic photoelectric device according to example embodiments.

Example embodiments will hereinafter be described in detail, and may be more easily performed by those who have common knowledge in the related art. However, this disclosure may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numerals throughout the specification.

As used herein, when specific definition is not otherwise provided, the term "substituted" refers to one substituted with a substituent selected from a halogen (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid or a salt thereof, a $C_1$ to $C_{20}$ alkyl group, a $C_1$ to $C_{20}$ alkoxy group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_{20}$ heteroalkyl group, a $C_1$ to $C_{20}$ heteroaryl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof, instead of hydrogen of a compound.

As used herein, when specific definition is not otherwise provided, the term "hetero" refers to one including 1 to 3 heteroatoms selected from N, O, S, and P.

Hereinafter, a compound for an organic photoelectric device according to example embodiments is described.

A compound for an organic photoelectric device according to example embodiments is represented by Chemical Formula 1.

[Chemical Formula 1]

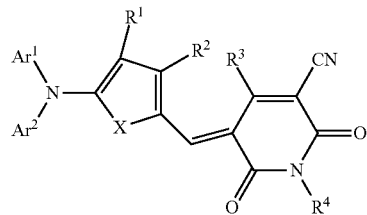

In Chemical Formula 1,

X is one of S, Se, Te, S(=O), S(=O)$_2$, and SiR$^a$R$^b$ (wherein each of R$^a$ and R$^b$ are one of hydrogen and $C_1$ to $C_6$ alkyl group), each of Ar$^1$ and Ar$^2$ are independently one of a substituted or unsubstituted $C_6$ to $C_{30}$ aryl group and a substituted or unsubstituted $C_4$ to $C_{20}$ heteroaryl group, each of R$^1$ and R$^2$ are independently one of hydrogen, a substituted or unsubstituted $C_1$ to $C_6$ alkyl group, a substituted or unsubstituted $C_6$ to $C_{10}$ aryl group, and a substituted or unsubstituted $C_4$ to $C_8$ heteroaryl group, and each of R$^3$ and R$^4$ are independently one of a substituted or unsubstituted $C_1$ to $C_6$ alkyl group and a substituted or unsubstituted $C_6$ to $C_{10}$ aryl group.

In the Ar$^1$, Ar$^2$, R$^1$, R$^2$, R$^3$, and R$^4$, the term "substituted" refers to one substituted with a $C_1$ to $C_6$ alkyl group, a $C_1$ to $C_6$ haloalkyl group, a $C_1$ to $C_6$ alkoxy group, or a halogen (F, Br, Cl, or I).

The compound may have 6 or 7 aromatic rings therein. When the number of the aromatic rings is 6 or 7, selective absorption in a green wavelength region may be improved.

Ar$^1$ and Ar$^2$ may each independently be a substituted or unsubstituted $C_6$ to $C_{30}$ aryl group where aromatic rings are fused to each other, or a substituted or unsubstituted $C_4$ to $C_{20}$ heteroaryl group, for example, a substituted or unsubstituted $C_6$ to $C_{30}$ aryl group. That is, when a single bond or other linking groups are present between the aromatic rings to link the aromatic rings group, a conjugation structure may be broken and a desirable conjugation length is not provided.

At least one of Ar$^1$ and Ar$^2$ may be a naphthyl group or an anthracenyl group. When at least one of Ar$^1$ and Ar$^2$ is a naphthyl group or an anthracenyl group, an intermolecular interaction is decreased, and thus aggregation among molecules in a film state is prevented or reduced. In this case, absorption selectivity in a green wavelength may be improved. When the Ar$^1$ and Ar$^2$ are an alkyl group or are fused to each other to provide an N-containing cycloalkyl group, instead of the aromatic group, the compound structure has planarity and thus a full width at half maximum (FWHM) of a light absorption curve may become too wide.

The semiconductor compound is a compound selectively absorbing light in a green wavelength region, and may have a maximum absorption wavelength ($\lambda_{max}$) at about 500 nm to about 600 nm, for example, at about 540 nm to about 560 nm.

The compound may show a light absorption curve having a full width at half maximum (FWHM) in a thin film state of about 50 nm to about 130 nm, for example, about 50 nm to about 110 nm, or about 50 nm to about 100 nm. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound may have a HOMO level about 5.0 to about 5.5 eV, and an energy bandgap of about 1.7 to about 2.3 eV. The compound having a HOMO level and an energy bandgap within the ranges may be used as a p-type semiconductor compound effectively absorbing light in a green wavelength region, and thus has high external quantum efficiency (EQE) and resultantly improves photoelectric conversion efficiency.

The compound may have a molecular weight of about 300 to about 1500, for example, about 350 to about 1200, or about 400 to about 900. When the compound has a molecular weight within the range, the crystallinity of the first compound and thermal decomposition during formation of a thin film by deposition may be inhibited.

The compound may have a melting point of greater than or equal to about 200° C., for example, greater than or equal to about 250° C., or greater than or equal to about 280° C. When the compound has a melting point within the range, a thin film may be stably deposited and an amount decomposed product is decreased, and thus an organic photoelectric device having improved photoelectric conversion performance is provided.

The compound may be a p-type semiconductor compound.

Hereinafter, an organic photoelectric device including the compound according to example embodiments is described with reference to drawings.

FIG. 1 is a cross-sectional view showing an organic photoelectric device according to example embodiments.

Referring to FIG. 1, an organic photoelectric device 100 according to example embodiments includes a first electrode 10 and a second electrode 20, and an active layer 30 interposed between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin monolayer or multilayer. When one of the first electrode 10 and the second electrode 20 is a non-light-transmitting electrode, it may be made of, for example, an opaque conductor such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound may act as a p-type semiconductor compound in the active layer 30.

The compound is a compound that selectively absorbs light in a green wavelength region, and the active layer 30 including the compound may have a maximum absorption wavelength ($\lambda_{max}$) at about 500 nm to about 600 nm, for example, about 540 nm to about 560 nm, which may selectively absorb light in a green wavelength region.

The active layer 30 may show a light absorption curve having a full width at half maximum (FWHM) in a thin film state of about 50 nm to about 130 nm, for example, about 50 nm to about 110 nm, or about 50 nm to about 100 nm. Accordingly, the active layer 30 has higher selectivity for light in a green wavelength region.

The active layer 30 may further include an n-type semiconductor compound for forming a pn junction.

The n-type semiconductor compound may be sub-phthalocyanine, fullerene or a fullerene derivative, thiophene or a thiophene derivative, or a combination thereof. The fullerene or fullerene derivative may be selected from a C60, C60 derivative, a C70, C70 derivative, and a combination thereof.

The sub-phthalocyanine may be represented by Chemical Formula 2.

[Chemical Formula 2]

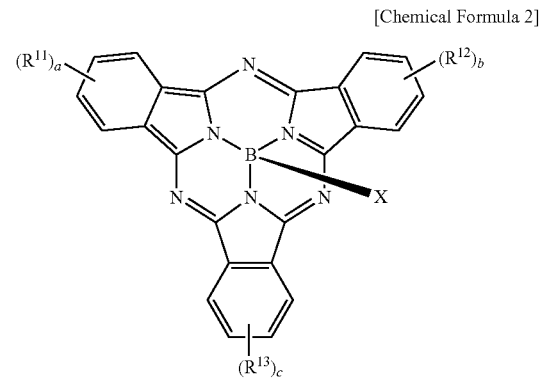

In Chemical Formula 2, each of $R^{11}$ to $R^{13}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a halogen-containing group, and a combination thereof, a, b, and c are integers ranging from 1 to 4, for example, 1 to 3, and X is a halogen, for example, one of F and Cl.

The halogen may refer to F, Cl, Br, or I, and the halogen-containing group may refer to an alkyl group where at least one of hydrogen is substituted with F, Cl, Br, or I.

The thiophene derivative may be, for example, represented by the following Chemical Formula 3 or Chemical Formula 4, but is not limited thereto.

[Chemical Formula 3]

[Chemical Formula 4]

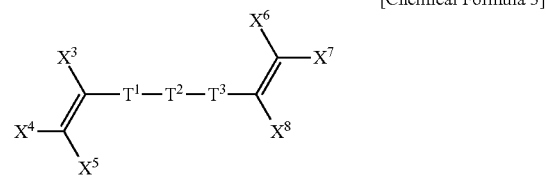

In Chemical Formulae 3 and 4, each of $T^1$, $T^2$, and $T^3$ are aromatic rings including substituted or unsubstituted thiophene moieties, each of $T^1$, $T^2$, and $T^3$ are independently present or are fused to each other, each of $X^3$ to $X^8$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a cyano group, and a combination thereof, and each of $EWG^1$ and $EWG^2$ are independently electron withdrawing groups.

For example, in the Chemical Formula 3, at least one of $X^3$ to $X^8$ is an electron withdrawing group, for example, a cyano group.

The active layer 30 may further include a second p-type semiconductor compound selectively absorbing green light. The p-type semiconductor compound may be a compound represented by Chemical Formula 5.

[Chemical Formula 5]

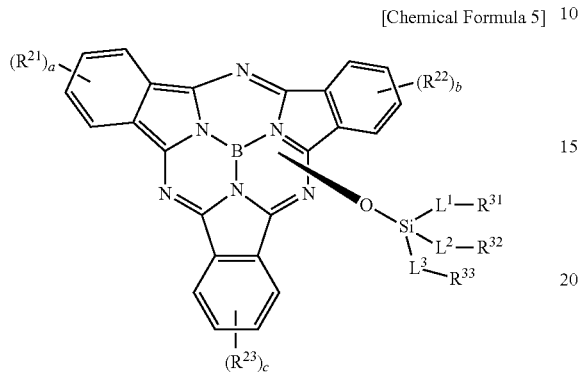

In Chemical Formula 5,

Each of $R^{21}$ to $R^{23}$ are independently one of hydrogen, a substituted or unsubstituted $C_1$ to $C_{30}$ aliphatic hydrocarbon group, a substituted or unsubstituted $C_6$ to $C_{30}$ aromatic hydrocarbon group, a substituted or unsubstituted $C_1$ to $C_{30}$ aliphatic heterocyclic group, a substituted or unsubstituted $C_2$ to $C_{30}$ aromatic heterocyclic group, a substituted or unsubstituted $C_1$ to $C_{30}$ alkoxy group, a substituted or unsubstituted $C_1$ to $C_{30}$ aryloxy group, a thio group, an alkylthio group, an arylthio group, a cyano group, a cyano-containing group, a halogen, a halogen-containing group, a substituted or unsubstituted sulfonyl group, a substituted or unsubstituted aminosulfonyl group, a substituted or unsubstituted arylsulfonyl group, and a combination thereof, or $R^{21}$ to $R^{23}$ are each independently present or are fused to each other to provide a ring, each of $L^1$ to $L^3$ are independently one of a single bond, a substituted or unsubstituted $C_1$ to $C_{30}$ alkylene group, a substituted or unsubstituted $C_6$ to $C_{30}$ arylene group, a divalent substituted or unsubstituted $C_3$ to $C_{30}$ heterocyclic group, and a combination thereof, each of $R^{31}$ to $R^{33}$ are independently one of a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a substituted or unsubstituted amine group, a substituted or unsubstituted $C_6$ to $C_{30}$ arylamine group, a substituted or unsubstituted silyl group, and a combination thereof, and each of a to c are independently integers ranging from 1 to 4, for example, 1 to 3.

The second p-type semiconductor compound selectively absorb green light may be included in an amount of about 500 to about 1500 parts by weight based on 100 parts by weight of the compound represented by the Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the compound of Chemical Formula 1 and the n-type semiconductor compound in a ratio of about 1:100 to about 100:1. The compounds may be included in a ratio ranging from about 1:50 to about 50:1 within the range, for example, about 1:10 to about 10:1, and for example, about 1:1. When the compounds have a composition ratio within the range, an exciton may be effectively produced and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm, for example, about 5 nm to about 300 nm. When the active layer 30 has a thickness within the range, the active layer may effectively absorb light, effectively separate holes from electrons, and deliver them, thereby effectively improving photoelectronic conversion efficiency. An optimal thickness of a thin film may be, for example, determined by an absorption coefficient of the active layer 30, and may be, for example, a thickness being capable of absorbing light of at least about 70% or more, for example about 80% or more, and for another example about 90%.

In the organic photoelectric device 100, when light enters from the first electrode 10 and/or second electrode 20, and when the active layer 30 absorbs light having a predetermined or given wavelength region, excitons may be produced from the inside. The excitons are separated into holes and electrons in the active layer 30, and the separated holes are transported to an anode that is one of the first electrode 10 and second electrode 20 and the separated electrons are transported to the cathode that is the other of and the first electrode 10 and second electrode 20 so as to flow a current in the organic photoelectric device.

Hereinafter, an organic photoelectric device according to example embodiments is described with reference to FIG. 2.

Figure 2:
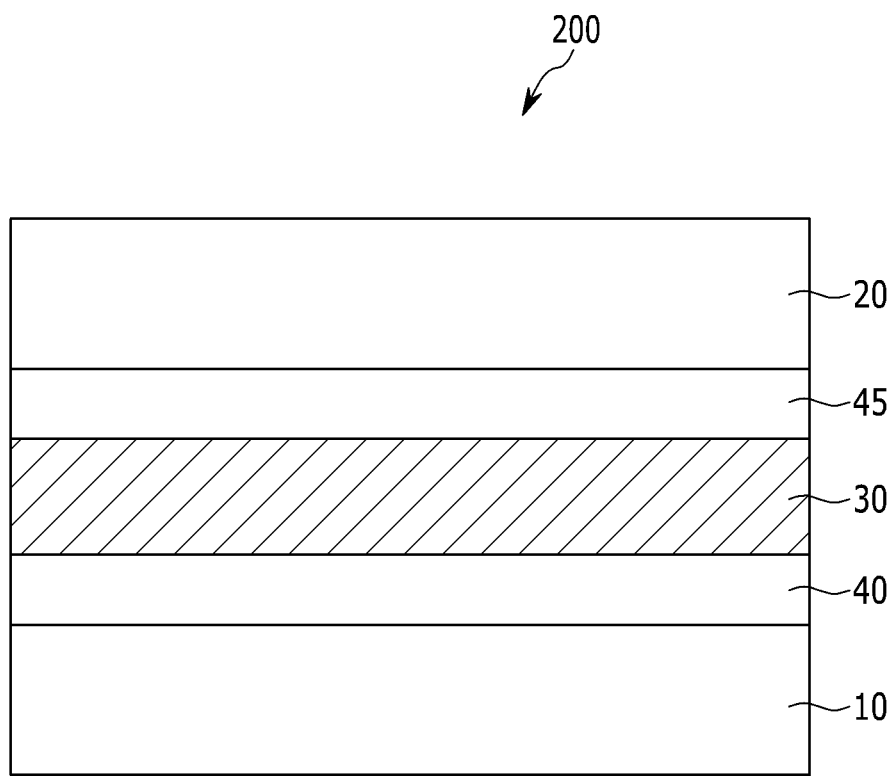
FIG. 2 is a cross-sectional view of an organic photoelectric device according to example embodiments.

FIG. 2 is a cross-sectional view showing an organic photoelectric device according to example embodiments.

Referring to FIG. 2, an organic photoelectric device 200 according to example embodiments includes a first electrode 10 and a second electrode 20 facing each other, and an active layer 30 interposed between the first electrode 10 and the second electrode 20, like the example embodiments illustrated in FIG. 1.

However, the organic photoelectric device 200 according to example embodiments further includes charge auxiliary layers 40 and 45 between the first electrode 10 and the active layer 30, and the second electrode 20 and the active layer 30, unlike the example embodiments illustrated in FIG. 1. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for preventing or reducing electron transport, an electron injection layer (EIL) for facilitating electron injection, an electron transport layer (ETL) for facilitating electron transport, and a hole blocking layer (HBL) for preventing or reducing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly (styrenesulfonate) (P EDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4''-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4''-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The organic photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
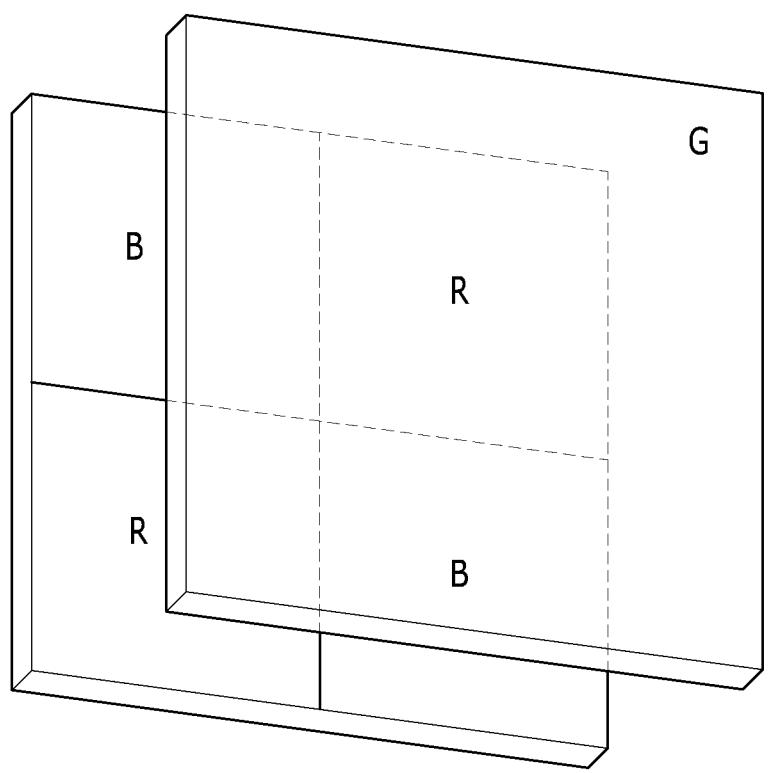
FIG. 3 is a schematic view showing an organic CMOS image sensor according to example embodiments.
Figure 4:
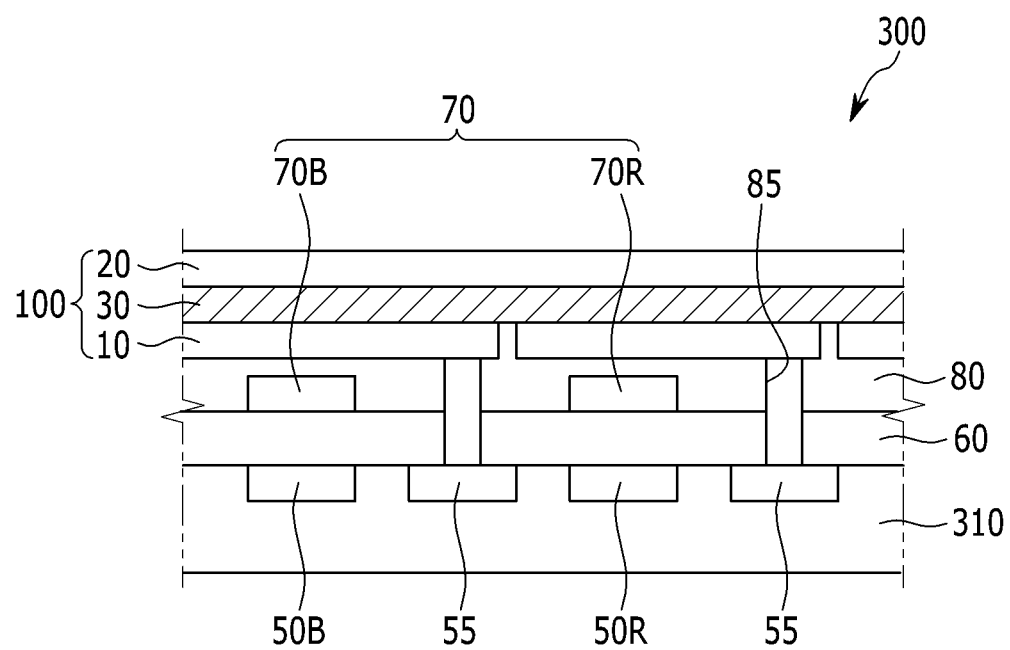
FIG. 4 is a cross-sectional view showing the organic CMOS image sensor of FIG. 3.

FIG. 3 is a schematic view of an organic CMOS image sensor according to example embodiments, and FIG. 4 is a cross-sectional view of the organic CMOS image sensor of FIG. 3.

Referring to FIGS. 3 and 4, an organic CMOS image sensor 300 according to example embodiments includes a semiconductor substrate 310 integrated with photo-sensing devices 50B and 50R, a transmission transistor (not shown), a charge storage 55, a lower insulation layer 60, a color filter layer 70, an upper insulation layer 80, and an organic photoelectric device 100.

The semiconductor substrate 310 may be a silicon substrate, and is integrated with the photo-sensing devices 50R and 50B, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected with the organic photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and a red filter 70R filled in the red pixel. In example embodiments, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be provided.

The upper insulation layer 80 is formed on the color filter layer 70. The upper insulation layer 80 eliminates a step caused by the color filter layer 70 and smoothes the surface. The upper insulation layer 80 and the lower insulation layer 60 may include a contact hole (not shown) exposing a pad, and a through-hole 85 exposing the charge storage 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs light in a green wavelength region and replaces a color filter of a green pixel.

When light enters from the second electrode 20, the light in a green wavelength region may be mainly absorbed in the active layer 30 and photoelectronically converted, while the light in the rest of the wavelength regions passes through first electrode 10 and may be sensed in the photo-sensing devices 50B and 50R.

As described above, the organic photoelectric devices selectively absorbing light in a green wavelength region are stacked and thereby a size of an image sensor may be decreased and a down-sized image sensor may be realized.

As described above, the compound represented by the Chemical Formula 1 may be used as a p-type or n-type semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased, and sensitivity may be increased.

Figure 5:
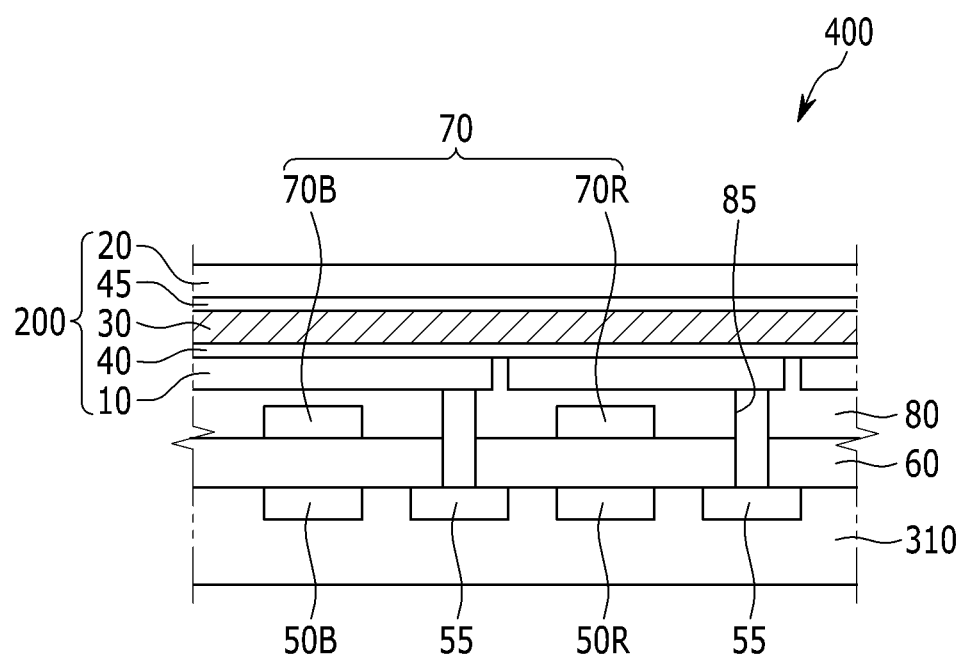
FIG. 5 is a schematic cross-sectional view showing an organic CMOS image sensor according to example embodiments.

In FIG. 4, the organic photoelectric device 100 of FIG. 1 is included, but it is not limited thereto, and thus the organic photoelectric device 200 of FIG. 2 may be applied in the same manner. FIG. 5 shows a structure of an image sensor having such a structure, and is a cross-sectional view of an organic CMOS image sensor 400 including the organic photoelectric device 200 in FIG. 2.

Figure 6:
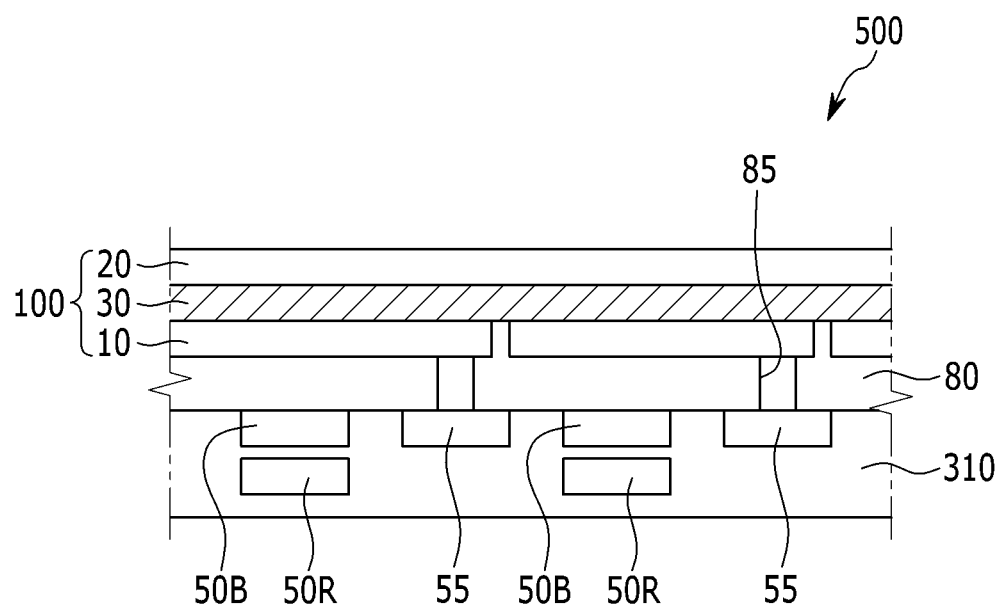
FIG. 6 is a schematic cross-sectional view showing an organic CMOS image sensor according to example embodiments.

FIG. 6 is a cross-sectional view showing an organic CMOS image sensor according to example embodiments.

Referring to FIG. 6, the organic CMOS image sensor 500 according to example embodiments includes a semiconductor substrate 310 integrated with photo-sensing devices 50B and 50R, a transmission transistor (not shown), a charge storage 55, an insulation layer 80, and an organic photoelectric device 100, like the example embodiments illustrated in FIGS. 4 and 5.

However, the organic CMOS image sensor 500 according to example embodiments includes the blue photo-sensing device 50B and the red photo-sensing device 50R that are stacked and does not include a color filter layer 70, unlike the example embodiments illustrated in FIGS. 4 and 5. The blue photo-sensing device 50B and the red photo-sensing device 50R are electrically connected with the charge storage, and the information of the charge storage 55 may be transferred by the transmission transistor (not shown). The blue photo-sensing device 50B and the red photo-sensing device 50R may selectively absorb light in each wavelength region depending on a stack depth.

As described above, the organic photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the organic photoelectric device 100 has improved green wavelength selectivity, and crosstalk caused by unnecessary absorption of light in a wavelength region except green may be decreased while increasing sensitivity.

In FIG. 6, the organic photoelectric device 100 of FIG. 1 is included, but it is not limited thereto, and thus the organic photoelectric device 200 of FIG. 2 may be applied in the same manner.

Figure 7:
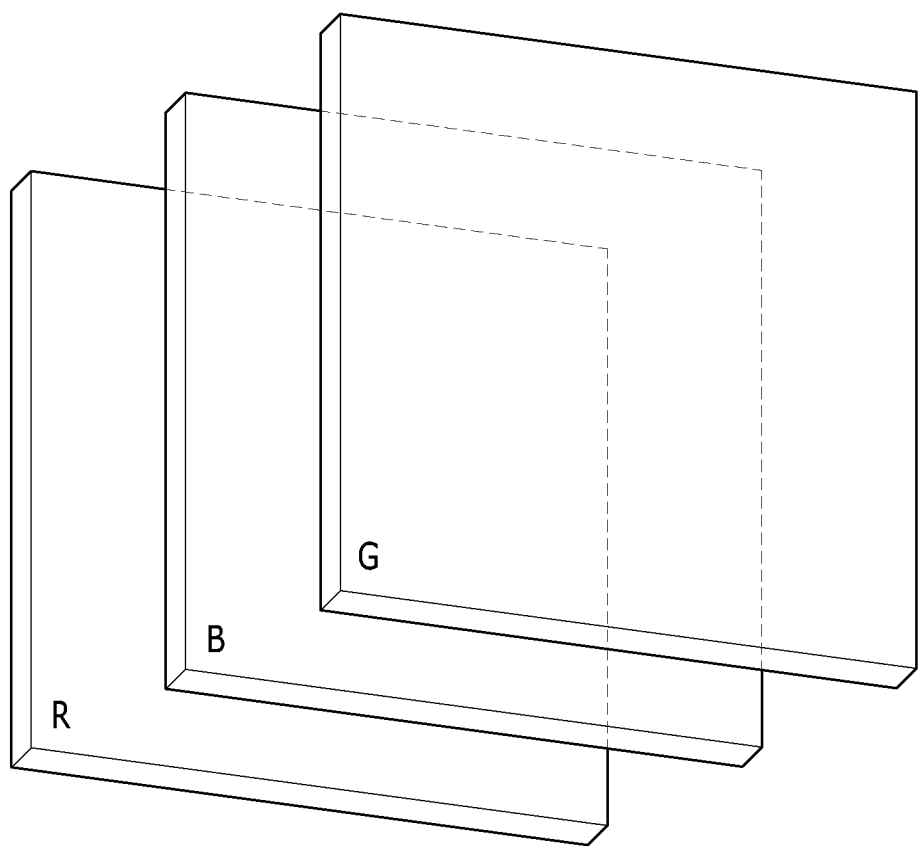
FIG. 7 is a schematic view showing an organic CMOS image sensor according to example embodiments.

FIG. 7 is a schematic view showing an organic CMOS image sensor according to example embodiments.

Referring to FIG. 7, the organic CMOS image sensor according to example embodiments includes a green photoelectric device (G) selectively absorbing light in a green wavelength region, a blue photoelectric device (B) selectively absorbing light in a blue wavelength region, and a red photoelectric device (R) selectively absorbing light in a red wavelength region that are stacked.

In the drawing, the red photoelectric device (R), the blue photoelectric device (B) and the green photoelectric device (G) are sequentially stacked, but the stack order may be changed without limitation.

The green photoelectric device may be the above organic photoelectric device 100, the blue photoelectric device may include electrodes facing each other and an active layer interposed therebetween and including an organic material selectively absorbing light in a blue wavelength region, and the red photoelectric device may include electrodes facing each other and an active layer interposed therebetween and including an organic material selectively absorbing light in a red wavelength region.

As described above, the organic photoelectric device selectively absorbing light in a green wavelength region, the organic photoelectric device selectively absorbing light in a red wavelength region, and the organic photoelectric device selectively absorbing light in a blue wavelength region are stacked, and thereby a size of an image sensor may be decreased and a down-sized image sensor may be realized.

The image sensor may be applied to various electronic devices, for example a mobile phone, a digital camera, and the like, but is not limited thereto.

Hereinafter, the present disclosure is illustrated in more detail with reference to examples. However, these examples are exemplary, and the present disclosure is not limited thereto.

SYNTHESIS EXAMPLE 1

Synthesis of the Compound Represented by Chemical Formula 1-1 ((E)-1,4-dimethyl-5-((5-(naphthalen-1-yl(phenyl)amino)thiophen-2-yl)methylene)-2,6-dioxo-1,2,5,6-tetrahydropyridine-3-carbonitrile)

[Chemical Formula 1-1]

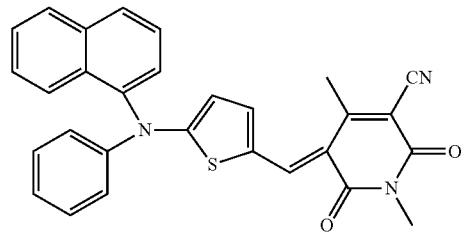

[Reaction Scheme 1]

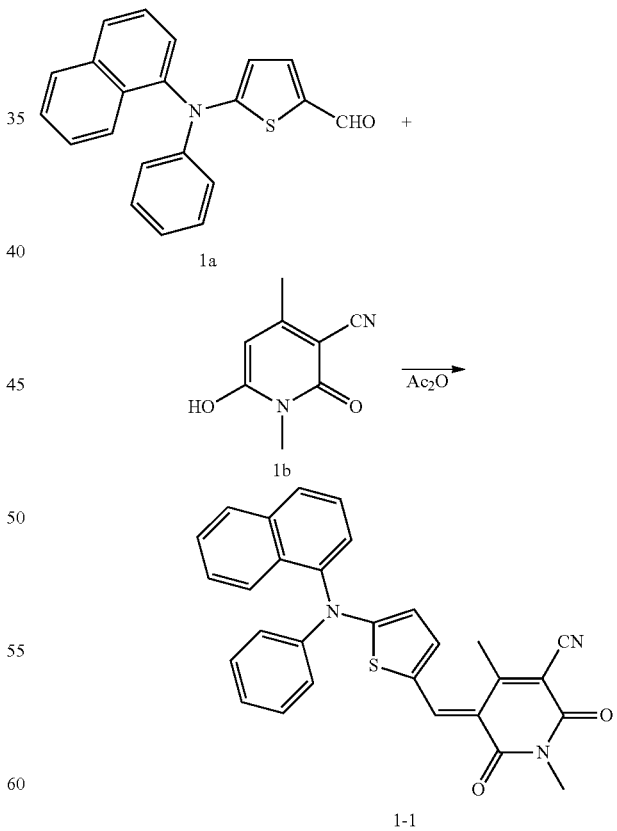

5-(naphthalen-1-yl(phenyl)amino)thiophene-2-carbaldehyde (a compound 1a, 1 mmol) and 6-hydroxy-1,4-dimethyl-2-oxo-1,2-dihydropyridine-3-carbonitrile (a compound 1b, 1 mmol) are mixed in acetic anhydride (Ac$_2$O, 0.5 mL), and the mixture is agitated at 100° C. for 30 minutes.

The resultant is cooled down to room temperature, hexane is added thereto, and a solid precipitated therein is collected through vacuum-filtering. The collected solid is dissolved in dichloromethane and separated with a mixed solution of dichloromethane and ethyl acetate through silica gel column chromatography. After removing a solvent from the separated solution, the obtained solid is recrystallized in a mixed solution of dichloromethane and hexane, obtaining a compound represented by the above Chemical Formula 1-1. The yield of the compound is 75%.

$^1$H-NMR (CDCl$_3$, 300 MHz): δ 6 8.07-8.02 (m, 2H), δ7.57-6.63 (m, 10H), δ7.60 (d, 1H), δ 7.50 (s, 1H), δ 6.36 (d, 1H), δ 3.23 (s, 3H), δ 2.21 (s, 3H). HRMS (ESI$^+$) Calculated for C$_{29}$H$_{22}$N$_3$O$_2$S [M+H$^+$]: 476.1433 Found: 476.1430.

SYNTHESIS EXAMPLE 2

Synthesis of the Compound Represented by Chemical Formula 1-2

[Chemical Formula 1-2]

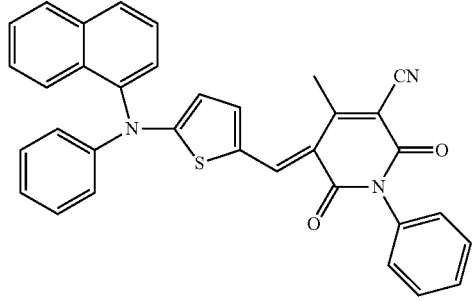

A compound represented by Chemical Formula 1-2 is synthesized according to the same method as Synthesis Example 1, except for using 6-hydroxy-4-methyl-2-oxo-1-phenyl-1,2-dihydropyridine-3-carbonitrile (1 mmol) instead of the compound 1 b. The yield of the compound is 75%.

$^1$H-NMR (CDCl$_3$, 300 MHz): δ 8.07-8.02 (m, 2H), δ 7.57-6.63 (m, 15H), δ 7.60 (d, 1H), δ 7.50 (s, 1H), δ 6.36 (d, 1H), δ 2.21 (s, 3H). HRMS (ESI$^+$) Calculated for C$_{34}$H$_{24}$N$_3$O$_2$S [M+H$^+$]: 538.1589 Found: 538.1585.

SYNTHESIS EXAMPLE 3

Synthesis of the Compound Represented by Chemical Formula 1-3

[Chemical Formula 1-3]

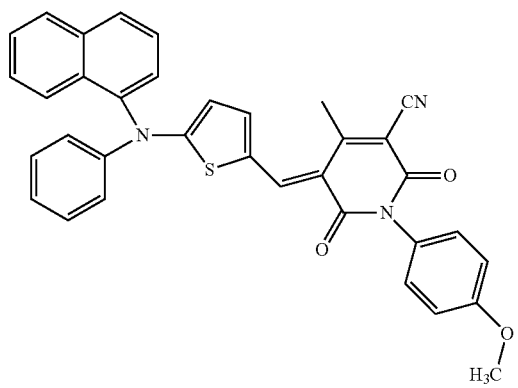

A compound represented by Chemical Formula 1-3 is synthesized according to the same method as Synthesis Example 1, except for using 6-hydroxy-1-(4-methoxyphenyl)-4-methyl-2-oxo-1,2-dihydropyridine-3-carbonitrile (1 mmol) instead of the compound 1 b. The yield of the compound is 73%.

$^1$H-NMR (CDCl$_3$, 300 MHz): δ 8.07-8.02 (m, 2H), δ 7.57-6.63 (m, 14H), δ 7.60 (d, 1H), δ 7.50 (s, 1H), δ 6.36 (d, 1H), δ 3.83 (s, 3H), δ 2.21 (s, 3H). HRMS (ESI$^+$) Calculated for C$_{35}$H$_{26}$N$_3$O$_3$S [M+H$^+$]: 568.1695 Found: 568.1693.

SYNTHESIS EXAMPLE 4

Synthesis of the Compound Represented by Chemical Formula 1-4

[Chemical Formula 1-4]

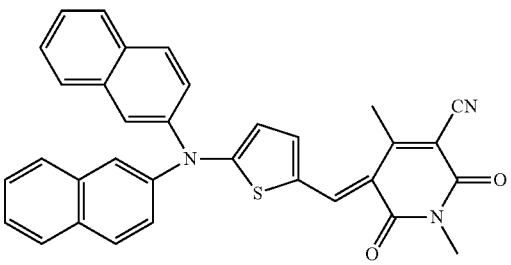

A compound represented by Chemical Formula 1-3 is synthesized according to the same method as Synthesis Example 1, except for using 5-(di(naphthalen-2-yl)amino)thiophene-2-carbaldehyde (1 mmol) instead of the compound 1a. The yield of the compound is 70%.

$^1$H-NMR (CDCl$_3$, 300 MHz): δ 7.88-7.36 (m, 14H), δ 7.60 (d, 1H), δ 7.50 (s, 1H), δ 6.36 (d, 1H), δ 3.23 (s, 3H), δ 2.21 (s, 3H). HRMS (ESI$^+$) Calculated for C$_{33}$H$_{24}$N$_3$O$_2$S [M+H$^+$]: 526.1589 Found: 526.1585.

SYNTHESIS EXAMPLE 5

Synthesis of the Compound Represented by Chemical Formula 1-5

[Chemical Formula 1-5]

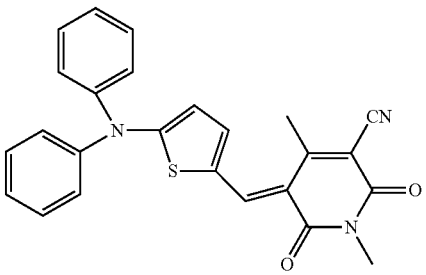

A compound represented by Chemical Formula 1-5 is synthesized according to the same method as Synthesis Example 1, except for using 5-(diphenylamino)thiophene-2-carbaldehyde (1 mmol) instead of the compound 1a. The yield of the compound is 75%.

¹H-NMR (CDCl₃, 300 MHz): δ 7.20-6.63 (m, 10H), δ 7.60 (d, 1H), δ 7.50 (s, 1H), δ 6.36 (d, 1H), δ 3.23 (s, 3H), δ 2.21 (s, 3H). HRMS (ESI⁺) Calculated for $C_{25}H_{20}N_3O_2S$ [M+H⁺]: 426.1276 Found: 426.1275.

SYNTHESIS EXAMPLE 6

Synthesis of the Compound Represented by Chemical Formula 1-6 ((E)-1,4-dimethyl-5-((5-(naphthalen-1-yl(phenyl)amino)selenophen-2-yl)methylene)-2,6-dioxo-1,2,5,6-tetrahydropyridine-3-carbonitrile)

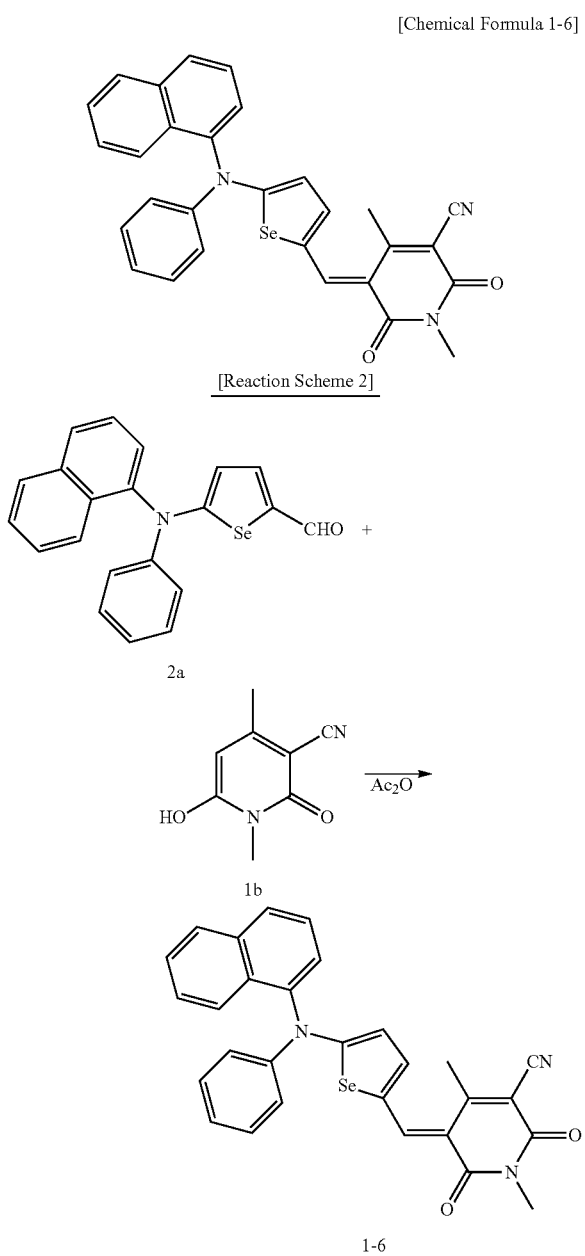

[Chemical Formula 1-6]

[Reaction Scheme 2]

A compound represented by Chemical Formula 1-6 is synthesized according to the same method as Synthesis Example 1, except for using 5-(naphthalen-1-yl(phenyl)amino)selenophene-2-carbaldehyde (2a) (1 mmol) instead of the compound 1a. The yield of the compound is 73%.

¹H-NMR (CDCl₃, 300 MHz): δ 8.07-8.02 (m, 2H), ε 7.57-6.29 (m, 10H), δ 7.36 (d, 1H), δ 7.14 (s, 1H), δ 6.59 (d, 1H), δ 3.23 (s, 3H), δ 2.58 (s, 3H). HRMS (ESI⁺) Calculated for $C_{29}H_{22}N_3O_2Se$ [M+H⁺]: 524.0877 Found: 524.0875.

COMPARATIVE SYNTHESIS EXAMPLE 1

Synthesis of the Compound Represented by Chemical Formula 1-7

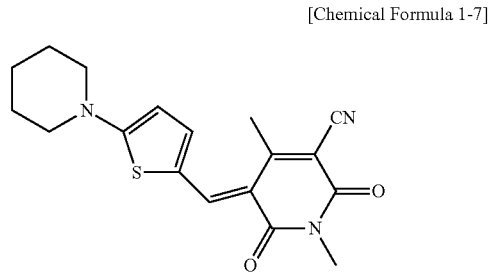 [SMILES: CC1=C(C#N)C(=O)N(C)C(=O)/C1=C/c1ccc(N2CCCCC2)s1]

[Chemical Formula 1-7]

A compound represented by Chemical Formula 1-7 is synthesized according to the same method as Synthesis Example 1, except for using 5-(piperidin-1-yl)thiophene-2-carbaldehyde (1 mmol) instead of the compound 1a. The yield of the compound is 75%.

¹H-NMR (CDCl₃, 300 MHz): δ 7.60 (d, 1H), δ 7.50 (s, 1H), δ 6.36 (d, 1H), δ 3.71 (m, 4H), δ 3.23 (s, 3H), δ 2.21 (s, 3H), δ 1.59-1.53 (m, 6H). HRMS (ESI⁺) Calculated for $C_{18}H_{20}N_3O_2S$ [M+H⁺]: 342.1276 Found: 342.1275.

COMPARATIVE SYNTHESIS EXAMPLE 2

Synthesis of the Compound Represented by Chemical Formula 1-8

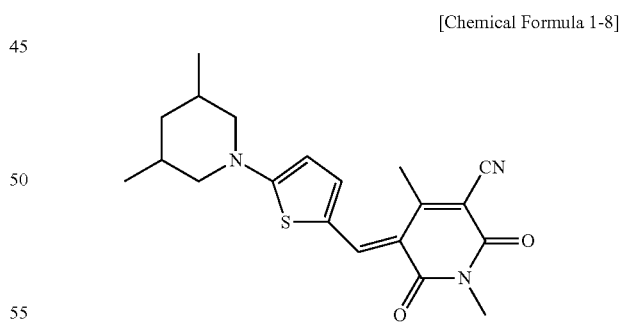

[Chemical Formula 1-8]

A compound represented by Chemical Formula 1-8 is synthesized according to the same method as Synthesis Example 1, except for using 5-(3,5-dimethylpiperidin-1-yl)thiophene-2-carbaldehyde (1 mmol) instead of the compound 1 a. The yield of the compound is 73%.

¹H-NMR (CDCl₃, 300 MHz): δ 7.60 (d, 1H), δ 7.50 (s, 1H), δ 6.36 (d, 1H), δ 3.23 (s, 3H), δ 3.04 (m, 2H), δ 2.79 (m, 2H), δ 2.21 (s, 3H), δ 1.67 (m, 2H), δ 1.54-1.29 (m, 2H), δ 96 (s, 6H). HRMS (ESI⁺) Calculated for $C20H24N3O2S$ [M+H⁺]: 370.1589 Found: 370.1585.

Light Absorption Characteristics Of Compounds Of Synthesis Examples 1 to 6 and Comparative Synthesis Examples 1 and 2

Light absorption characteristics depending on a wavelength of the compounds according to Synthesis Examples 1 to 6 and Comparative Synthesis Examples 1 and 2 are evaluated. Light absorption characteristics in a solution state and in a thin film state are evaluated.

Light absorption characteristics in a solution state are evaluated by respectively dissolving the compounds of Synthesis Examples 1 to 6 and Comparative Synthesis Examples 1 and 2 in dichloromethane with a concentration of $1.0 \times 10^{-5}$ mol/L.

Light absorption characteristics in a thin film are evaluated by thermally depositing each compound of Synthesis Examples 1 to 6 and Comparative Synthesis Examples 1 and 2 under a high vacuum ($<10^{-7}$ Torr) at a speed of 0.5-1.0 Å/s to respectively form a 70 nm-thick thin film and radiating ultraviolet (UV)-visible rays (UV-Vis) with Cary 5000 UV spectroscopy (Varian, Inc.). The results of Synthesis Examples 1 to 5 and Comparative Synthesis Examples 1 and 2 are shown in Table 1.

Thermal Stability of Compounds of Synthesis Examples 1 to 6 and Comparative Synthesis Examples 1 and 2

Thermal stability of the compounds according to Synthesis Examples 1 to 6 and Comparative Synthesis Examples 1 and 2 is evaluated by measuring thermal degradation temperatures. The thermal degradation temperature ($T_d$) indicates a temperature at which a compound starts to be decomposed and does not maintain its original molecular structure but is transformed. In general, since atoms in a molecule consisting of a compound are volatilized and lost into the air or vacuum at greater than or equal to the thermal degradation temperature, the thermal degradation temperature may be regarded as a temperature at which the initial weight of the compound is decreased by heat. Herein, the thermal degradation temperature is evaluated in a thermal gravimetric analysis (TGA) method. The results of Synthesis Examples 1 to 5 and Comparative Synthesis Examples 1 and 2 are provided in Table 1.

TABLE 1

| | $\lambda_{max}$ (nm) | | FWHM (nm) | | Energy level (film) | | |
|---|---|---|---|---|---|---|---|
| | solution | thin film | solution | thin film | HOMO (eV) | LUMO (eV) | $T_d$ (° C.) |
| Synthesis Example 1 | 547 | 563 | 47 | 95 | 5.65 | 3.66 | 246 |
| Synthesis Example 2 | 548 | 553 | 47 | 87 | 5.57 | 3.57 | 291 |
| Synthesis Example 3 | 548 | 558 | 47 | 70 | 5.53 | 3.51 | 285 |
| Synthesis Example 4 | 560 | 574 | 60 | 97 | 5.50 | 3.52 | 260 |
| Synthesis Example 5 | 549 | 546 | 53 | 125 | 5.57 | 3.62 | 230 |
| Comparative Synthesis Example 1 | 539 | 500 | 25 | 133 | 5.12 | 3.06 | 240 |
| Comparative Synthesis Example 2 | 539 | 491 | 25 | 125 | 5.10 | 3.04 | 273 |

Referring to Table 1, the compounds of Synthesis Examples 1 to 5 and Comparative Synthesis Examples 1 and 2 show almost the same light absorption characteristics in a solution state. However, comparing light absorption characteristics in a thin film, the compounds of Synthesis Examples 1 to 5 show a maximum absorption wavelength in a green wavelength region (e.g., 530 nm to 575 nm) and a narrower full width at half maximum (FWHM) than the compounds of Comparative Synthesis Examples 1 and 2. In particular, the compounds of Comparative Synthesis Examples 1 and 2 show a narrower full width at half maximum (FWHM) in solution states but a wider full width at half maximum (FWHM) in thin film states, since molecules of the compounds are aggregated due to structural planarity of the thin films. Accordingly, the compounds of Synthesis Examples 1 to 5 show improved green wavelength selectivity compared with the compounds of Comparative Synthesis Examples 1 and 2.

In addition, referring to Table 1, the compounds of Synthesis Examples 1 to 5 show a HOMO energy level of 5.5 to 5.6 eV in a thin film state and easily transport separated holes to neighboring charge auxiliary layers 40 and 45 having a HOMO energy level of 5.5 eV or so, and thus may increase photoelectric conversion efficiency. When the charge auxiliary layers 40 and 45 are added to a photoelectric conversion device, the compounds of Synthesis Examples 1 to 5 due to the above characteristics may realize much higher photoelectric conversion efficiency than the compounds of Comparative Synthesis Examples 1 and 2 having a HOMO energy level of 5.10 eV or so in a thin film state.

In addition, the compounds of Synthesis Examples 1 to 5 and Comparative Synthesis Examples 1 and 2 show a difference between LUMO and HOMO energy levels of about 2.0 eV or so in a thin film state, and thus a similar energy bandgap.

Furthermore, the compounds of Synthesis Examples 1 to 5 have a high thermal degradation temperature and thus have improved thermal stability.

EXAMPLE 1

An about 100 nm-thick anode is formed by sputtering ITO on a glass substrate, and a 10 nm-thick molybdenum oxide ($MoO_x$, $0<x\leq3$) thin film is laminated as a charge auxiliary layer thereon. Subsequently, an 85 nm-thick active layer is formed by codepositing the compound of Synthesis Example 1 (a p-type semiconductor compound) and C60 (an n-type semiconductor compound) in a thickness ratio of 1:1 on the molybdenum oxide ($MoO_x$) thin film. On the active layer, an 80 nm-thick cathode is formed by sputtering aluminum (Al), manufacturing an organic photoelectric device.

EXAMPLES 2 to 5

Each organic photoelectric device according to Examples 2 to 5 is manufactured according to the same method as Example 1, except for using each compound according to Synthesis Examples 2 to 5, instead of the compound of the Synthesis Example 1.

External Quantum Efficiency (EQE)

External quantum efficiency (EQE) of the organic photoelectric devices according to Examples 1 to 6 depending on wavelength and voltage is evaluated.

The external quantum efficiency is measured by using an IPCE measurement system (McScience Co., Ltd. Korea). First of all, the IPCE measurement system is calibrated by using a Si photodiode (Hamamatsu Photonics K.K., Japan), the organic photoelectric devices of Examples 1 to 6 are then respectively mounted thereon, and their external quantum efficiency in a wavelength region of about 350 to 750 nm is determined. Of these, the external quantum efficiency of the organic photoelectric device according to Example 1 is shown in FIGS. 8 and 9.

Figure 8:
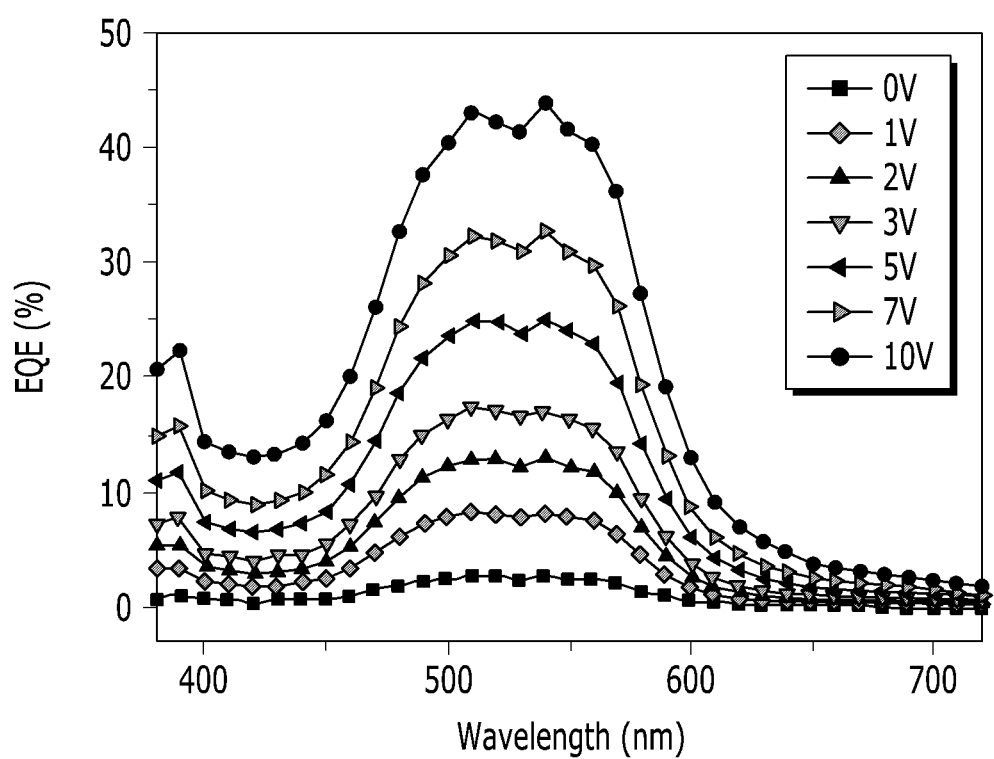
FIG. 8 shows external quantum efficiency (EQE) depending on a voltage of the organic photoelectric device of Example 1.
Figure 9:
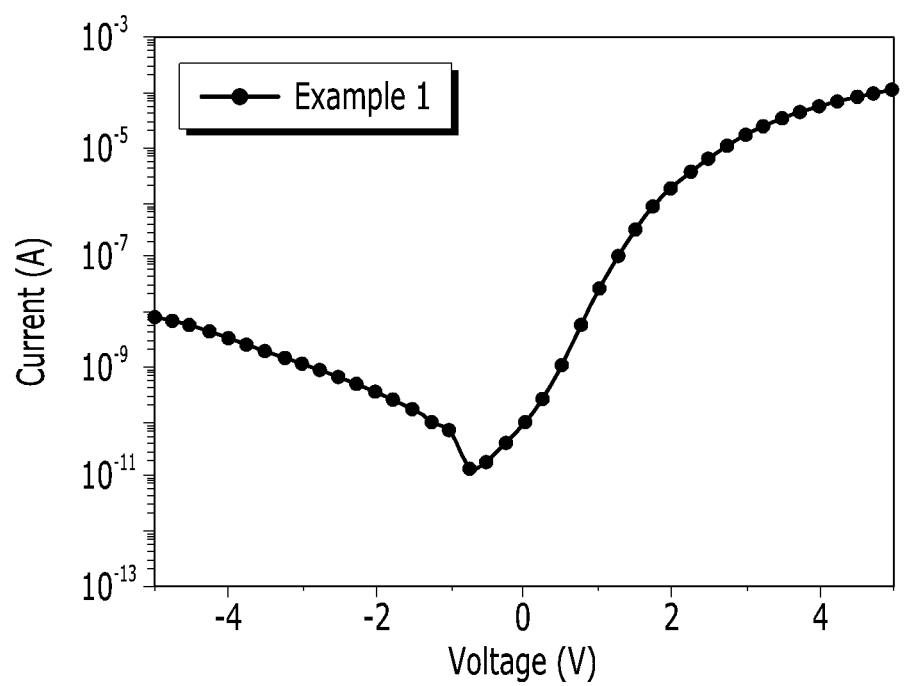
FIG. 9 shows voltage-current characteristics of the organic photoelectric device of Example 1.

FIG. 8 shows external quantum efficiency (EQE) depending on a voltage of the organic photoelectric device of Example 1, and FIG. 9 shows voltage-current characteristics of the organic photoelectric device of Example 1.

Referring to FIGS. 8 and 9, the organic photoelectric devices according to Example 1 show improved external quantum efficiency (EQE) in a green wavelength region of about 500 nm to 600 nm.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. A compound for an organic photoelectric device represented by Chemical Formula 1:

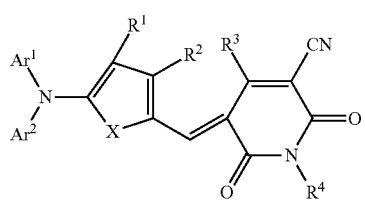

[Chemical Formula 1]

wherein, in Chemical Formula 1,
X is,
each of $Ar^1$ and $Ar^2$ are independently one of a substituted or unsubstituted $C_6$ to $C_{30}$ aryl group and a substituted or unsubstituted $C_4$ to $C_{20}$ heteroaryl group,
each of $R^1$ and $R^2$ are independently one of hydrogen, a substituted or unsubstituted $C_1$ to $C_6$ alkyl group, a substituted or unsubstituted $C_6$ to $C_{10}$ aryl group, and a substituted or unsubstituted $C_4$ to $C_8$ heteroaryl group, and
each of $R^3$ and $R^4$ are independently one of a substituted or unsubstituted $C_1$ to $C_6$ alkyl group and a substituted or unsubstituted $C_6$ to $C_{10}$ aryl group,
wherein at least one of $Ar^1$ and $Ar^2$ is one of a naphthyl group or an anthracenyl group, and
wherein the compound has a maximum absorption wavelength (λmax) of about 500 nm to about 600 nm.

2. The compound of claim 1, wherein the compound has 6 or 7 aromatic rings.

3. The compound of claim 1, wherein the compound shows a light absorption curve having a full width at half maximum (FWHM) in a thin film state of about 50 nm to about 130 nm.

4. The compound of claim 3, wherein the compound shows a light absorption curve having a full width at half maximum (FWHM) in a thin film state of about 50 nm to about 100 nm.

5. The compound of claim 1, wherein the compound is a p-type semiconductor compound.

6. An organic photoelectric device comprising:
a first electrode and a second electrode facing each other, and
an active layer between the first electrode and the second electrode, the active layer including a compound represented by Chemical Formula 1:

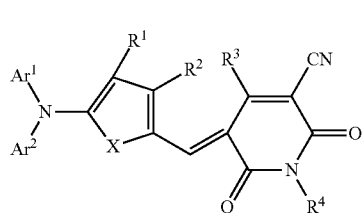

[Chemical Formula 1]

wherein, in Chemical Formula 1,
X is
each of $Ar^1$ and $Ar^2$ are independently one of a substituted or unsubstituted $C_6$ to $C_{30}$ aryl group and a substituted or unsubstituted $C_4$ to $C_2$ heteroaryl group,
each of $R^1$ and $R^2$ are independently one of hydrogen, a substituted or unsubstituted $C_1$ to $C_6$ alkyl group, a substituted or unsubstituted $C_6$ to $C_{10}$ aryl group, and a substituted or unsubstituted $C_4$ to $C_8$ heteroaryl group, and
each of $R^3$ and $R^4$ are independently one of a substituted or unsubstituted $C_1$ to $C_6$ alkyl group and a substituted or unsubstituted $C_6$ to $C_{10}$ aryl group,
wherein at least one of $Ar^1$ and $Ar^2$ is one of a naphthyl group or an anthracenyl group, and
wherein the compound has a maximum absorption wavelength (λmax) of about 500 nm to about 600 nm.

7. The organic photoelectric device of claim 6, wherein the compound has 6 or 7 aromatic rings.

8. The organic photoelectric device of claim 6, wherein the compound shows a light absorption curve having a full width at half maximum (FWHM) in a thin film state of about 50 nm to about 130 nm.

9. The organic photoelectric device of claim 6, wherein the compound shows a light absorption curve having a full width at half maximum (FWHM) in a thin film state of about 50 nm to about 100 nm.

10. The organic photoelectric device of claim 6, wherein the compound is a p-type semiconductor compound.

11. An image sensor comprising the organic photoelectric device of claim 6.

12. The image sensor of claim 11, further comprising:
a semiconductor substrate integrated with a plurality of first photo-sensing devices sensing light in a blue wavelength region and a plurality of second photo-sensing devices sensing light in a red wavelength region,
wherein the organic photoelectric device is on the semiconductor substrate and selectively absorbs light in a green wavelength region.

13. The image sensor of claim 12, wherein the plurality of first photo-sensing devices and the plurality of second photo-sensing devices are stacked in a vertical direction on the semiconductor substrate.

14. The image sensor of claim 12, further comprising:
a color filter layer between the semiconductor substrate and the organic photoelectric device, the color filter layer including a blue filter selectively absorbing light in a blue wavelength region and a red filter selectively absorbing light in a red wavelength region.

15. The image sensor of claim 11, wherein the organic photoelectric device is a green photoelectric device, further comprising:
a blue photoelectric device selectively absorbing light in a blue wavelength region; and
a red photoelectric device selectively absorbing light in a red wavelength region,
wherein the organic photoelectric device, a blue photoelectric device and a red photoelectric device are sequentially stacked.

16. An electronic device comprising the image sensor of claim 11.

17. A compound for an organic photoelectric device represented by Chemical Formula 1:

[Chemical Formula 1]

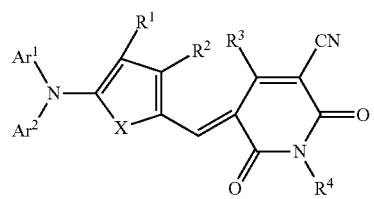

wherein, in Chemical Formula 1,
X is one of Se, Te, S(=O), S(=O)$_2$, and SiR$^a$R$^b$ (wherein each of R$^a$ and R$^b$ are one of hydrogen and a C$_1$ to C$_6$ alkyl group),
each of Ar$^1$ and Ar$^2$ are independently one of a substituted or unsubstituted C$_6$ to C$_{30}$ aryl group and a substituted or unsubstituted C$_4$ to C$_{20}$ heteroaryl group,
each of R$^1$ and R$^2$ are independently one of hydrogen, a substituted or unsubstituted C$_1$ to C$_6$ alkyl group, a substituted or unsubstituted C$_6$ to C$_{10}$ aryl group, and a substituted or unsubstituted C$_4$ to C$_8$ heteroaryl group, and
each of R$^3$ and R$^4$ are independently one of a substituted or unsubstituted C$_1$ to C$_6$ alkyl group and a substituted or unsubstituted C$_6$ to C$_{10}$ aryl group.

18. An organic photoelectric device comprising:
a first electrode and a second electrode facing each other, and
an active layer between the first electrode and the second electrode, the active layer including a compound represented by Chemical Formula 1:

[Chemical Formula 1]

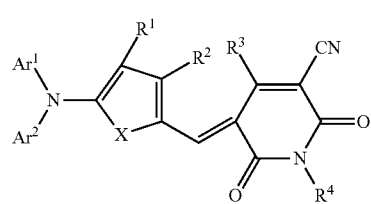

wherein, in Chemical Formula 1,
X is one of Se, Te, S(=O), S(=O)$_2$, and SiR$^a$R$^b$ (wherein R$^a$ and R$^b$ are one of hydrogen and a C$_1$ to C$_6$ alkyl group),
each of Ar$^1$ and Ar$^2$ are independently one of a substituted or unsubstituted C$_6$ to C$_{30}$ aryl group and a substituted or unsubstituted C$_4$ to C$_{20}$ heteroaryl group,
each of R$^1$ and R$^2$ are independently one of hydrogen, a substituted or unsubstituted C$_1$ to C$_6$ alkyl group, a substituted or unsubstituted C$_6$ to C$_{10}$ aryl group, and a substituted or unsubstituted C$_4$ to C$_8$ heteroaryl group, and
each of R$^3$ and R$^4$ are independently one of a substituted or unsubstituted C$_1$ to C$_6$ alkyl group and a substituted or unsubstituted C$_6$ to C$_{10}$ aryl group.

* * * * *